(12) United States Patent
Kjelden

(10) Patent No.: US 10,385,094 B2
(45) Date of Patent: Aug. 20, 2019

(54) COLOSTRUM SOLID EXTRACTION PROCESS

(71) Applicant: Dustin Kjelden, Brookings, SD (US)

(72) Inventor: Dustin Kjelden, Brookings, SD (US)

(*) Notice: Subject to any disclaimer, the term of this patent is extended or adjusted under 35 U.S.C. 154(b) by 131 days.

(21) Appl. No.: 15/660,440

(22) Filed: Jul. 26, 2017

(65) Prior Publication Data

US 2019/0031711 A1    Jan. 31, 2019

(51) Int. Cl.
*C07K 1/14* (2006.01)
*C07K 14/47* (2006.01)
*A23J 3/08* (2006.01)

(52) U.S. Cl.
CPC ............... *C07K 1/145* (2013.01); *A23J 3/08* (2013.01); *C07K 14/47* (2013.01)

(58) Field of Classification Search
None
See application file for complete search history.

(56) References Cited

U.S. PATENT DOCUMENTS

| 5,147,548 A | 9/1992 | Hies et al. |
| 5,707,678 A | 1/1998 | Gregory |
| 6,096,870 A | 8/2000 | Mozaffar et al. |
| 6,288,222 B1 | 9/2001 | Roth et al. |
| 6,426,109 B1 | 7/2002 | Ehsani et al. |
| 8,252,341 B2 | 8/2012 | Brazeau |
| 2003/0026845 A1 | 2/2003 | Etzel et al. |
| 2005/0175597 A1 | 8/2005 | Rawlin et al. |

FOREIGN PATENT DOCUMENTS

WO    WO2009135306    11/2009

*Primary Examiner* — Suzanne M Noakes

(57) ABSTRACT

A colostrum solid extraction process utilizes rennet coagulation prior to pH adjustment to alter the protein profile resulting in an animal feed supplement which enhances feed efficiency and general health. Rennet coagulation is used to produce extracted whey from colostrum. A pH of the extracted whey is adjusted by cooling the extracted whey to below 70 degrees Fahrenheit, adding an first solution to lower the pH of the extracted whey to 4.2 pH, adding a second solution to lower the pH of the extracted whey to 2.5 pH, agitating the extracted whey after reaching 2.5 pH, resting the extracted whey after agitation, and adding a third solution to raise the pH of the extracted whey to 4.2 pH.

17 Claims, No Drawings

COLOSTRUM SOLID EXTRACTION PROCESS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to protein extraction processes and more particularly pertains to a new extraction process in which pH is adjusted subsequent to separation to alter extracted protein effect in the final product.

BRIEF SUMMARY OF THE INVENTION

An embodiment of the disclosure meets the needs presented above by generally comprising a process using rennet coagulation to produce extracted whey from colostrum. A pH of the extracted whey is adjusted by cooling the extracted whey to below 70 degrees Fahrenheit, adding an first solution to lower the pH of the extracted whey to 4.2 pH, adding a second solution to lower the pH of the extracted whey to 2.5 pH, agitating the extracted whey after reaching 2.5 pH, resting the extracted whey after agitation, and adding a third solution to raise the pH of the extracted whey to 4.2 pH.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

(none)

DETAILED DESCRIPTION OF THE INVENTION

The colostrum solid extraction process generally comprises a multiple step process. The process will produce approximately a 75% yield such that for every 100 gallons of colostrum approximately 75 gallons of liquid whey will be produced. The liquid whey in turn will produce approximately 65 pounds of dry powder or 50 gallons of liquid final product. The colostrum is typically obtained through commercial markets in a frozen condition in buckets which may be stored until used for the process herein. The colostrum is initially inspected by removal of a lid on the bucket to permit organoleptic inspection. Anything atypical including but not limited to color and smell may be rejected. Colostrum not rejected in the initial organoleptic inspection is removed from the bucket into a thawing tank. The colostrum in the thawing tank is heated to between 45 and 55 degrees Fahrenheit. Thawing is defined as being complete when no visible ice chunks are present. The thawing produces pooled colostrum within the thawing tank. The volume and final temperature of the pooled colostrum is recorded prior to the step of separation.

The thawed and pooled colostrum is tested using a conventional colostrometer testing based on density of the colostrum. The reading on the conventional colostrumeter is recorded and the thawed and pooled colostrum is transferred through initial stage transfer lines to a separation tank where the thawed and pooled colostrum is heat treated and separated. The thawed and pooled colostrum is filtered when transferred to the separation tank by use of a filter sock attached to the transfer lines. The filtered colostrum is further heat treated within the separation tank to between 150 degrees Fahrenheit and 152 degrees Fahrenheit with 151 degrees Fahrenheit being the target temperature. The heated filtered colostrum is then separated using a conventional centrifugal separator. The casein is removed through rennet coagulation and draining of the whey as opposed to using an acid coagulation method. The use of rennet coagulation produces a different protein profile within the whey as a starting point for the later steps within the process. The whey is then clarified through subsequent centrifugal separation and allowed to cool to less than 45 degrees Fahrenheit if the final product be liquid and to 120 degrees Fahrenheit if the final product is to be dried into a powder form.

The heated and separated colostrum is physically separated into cream and skim milk components. The skim component is tested for pH. The cream component is moved into a new tank and the skim milk component is moved into a large cheese vat via clean skim milk transfer lines. A large cheese vat is one capable of holding approximately 45,000 pounds. The skim milk component in the cheese vat is curded by conventional processes and any related calculations may be recorded. When the curd produced is firmly set, the curd is stirred and the cheese vat temperature is raised to 101 to 102 degrees Fahrenheit. The temperature of the stirred curd is recorded. Whey separated from the curd in the curding process is transferred to a vat using a separator to also remove curd fines. The whey is heat treated by heating to 151 degrees Fahrenheit. A sock filter is used when transferring the heat treated whey to a holding vessel via a whey transfer line. The holding vessel is a generic term for the vessel being used as different processes are incorporated for liquid and powder forms of the final product. Particular characteristics of the holding vessel utilized may differ depending on the requirements of the steps described further below.

For a dry final product, the heat treated whey is heated again for pasteurization in a batch pasteurizer vat to a minimum of 145.0 degrees Fahrenheit. When the target temperature is reached a timer is set for a minimum of 30 minutes. The heated whey remains in the batch pasteurizer vat without removing the lid for a minimum of 30 minutes. After expiration of the minimum of 30 minutes, tank and air heating of the batch pasteurizing vat is shut off. For proper product production the temperature of the heated whey must remain at or above 145 degrees Fahrenheit for the minimum 30 minute hold time and the air temperature must remain at or above 150 degrees Fahrenheit for the minimum 30 minute hold time. After ten minutes of cooling time, a sterile sample of the pasteurized whey is removed to a container which is then placed into a larger vessel of cold water for testing which may be done at a separate test lab.

The pH of the whey is adjusted in a multiple step process after coagulation. This is done after the above second heating of the heat treated whey for a dry product, or without the above second heating of the heat treated whey when producing a liquid final product. The whey, being unpasteurized for the liquid final product or pasteurized for the dry final product, is allowed to cool to below 70 degrees Fahrenheit, an initial pH reading is measured, and may be recorded. Using a 1:9 acetic/water solution, the pH of the whey is lowered to 4.2 pH. The amount of acetic/water solution used per gallon of whey to lower the pH is recorded. The pH of the whey is then further lowered to 2.5 pH using a 1:6 hydrochloric acid/water solution. Upon reaching a pH of 2.5, the amount of hydrochloric acid/water solution per gallon used is recorded and the whey is agitated for one hour. After agitation, the whey sits for an hour and then the pH is raised back to 4.2 using a 1:10 caustic sodium hydroxide (50%)/water solution. The whey is not filtered after the pH is raised back to 4.2.

For the liquid final product, the whey is filtered using a 0.2 micron filter. 2.0 grams of Ethylenediaminetetraacetic acid (EDTA) and 15.2 grams of sodium benzoate are added per 1.0 gallons of 0.2 micron permeate. The liquid final product may then be bottled or otherwise packaged into tubes or another conventional container.

For a dry final product the pH adjusted whey is pumped into a clean silo after the pH adjusted whey has cooled to 40 degrees Fahrenheit. The pH adjusted whey is then dried in a conventional manner to produce the dry final product.

The final product is used as a supplement in animal feed to enhance feed efficiency and general health in the animals ingesting the animal feed.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A colostrum solid extraction process comprising the steps of:
   heat treating colostrum above 70 degrees Fahrenheit;
   separating the heated colostrum with a centrifugal separator;
   removing casein to produce extracted whey;
   adjusting a pH of the extracted whey by cooling of the extracted whey to below 70 degrees Fahrenheit, adding an first solution to lower the pH of the extracted whey to 4.2 pH, adding a second solution to lower the pH of the extracted whey to 2.5 pH;
   agitating said extracted whey after reaching 2.5 pH;
   resting said extracted whey after agitation; and
   adding a third solution to raise the pH of the extracted whey to 4.2pH.

2. The process of claim 1, wherein said first solution is an acetic/water solution.

3. The process of claim 2, wherein said acetic water solution is one part acetic acid to nine parts water.

4. The process of claim 1, wherein said second solution is a hydrochloric acid and water solution.

5. The process of claim 4, wherein said hydrochloric acid and water solution is one part hydrochloric acid to six parts water.

6. The process of claim 1, wherein said extracted whey is agitated for at least one hour.

7. The process of claim 1, wherein said step of resting said extracted whey after agitation comprises resting said whey for at least one hour after agitation.

8. The process of claim 1, wherein said third solution is a caustic sodium hydroxide and water solution.

9. The process of claim 8, wherein a concentration of said caustic sodium hydroxide and water solution is 50%.

10. The process of claim 9, wherein said caustic hydroxide and water solution is one part caustic sodium hydroxide to ten parts water.

11. The process of claim 10, the steps of the process further comprising the steps of:
    filtering said extracted whey after adding said caustic hydroxide and water solution through a filter; and
    adding 2.0 grams of Ethylenediaminetetraacetic acid and 15.2 grams of sodium benzoate per 1.0 gallons of a liquid permeating said filter.

12. The process of claim 11, the steps of the process further comprising a step of bottling of said liquid permeating said filter after addition of said Ethylenediaminetetraacetic acid and said sodium benzoate.

13. The process of claim 11, wherein said filter is a 0.2 micron filter.

14. The process of claim 1, the steps of the process further comprising the steps of:
    cooling said adjusted whey after adding said caustic hydroxide solution to 40degrees Fahrenheit; and
    drying said adjusted whey to produce a powder.

15. A colostrum solid extraction process comprising the steps of:
- heat treating colostrum above 70 degrees Fahrenheit;
- separating the heated colostrum with a centrifugal separator;
- removing casein to produce extracted whey;
- adjusting a pH of the extracted whey by cooling of the extracted whey to below 70 degrees Fahrenheit, adding an first solution to lower the pH of the extracted whey to 4.2 pH, said first solution being an acetic/water solution, said acetic water solution being one part acetic acid to nine parts water, adding a second solution to lower the pH of the extracted whey to 2.5 pH, said second solution being a hydrochloric acid and water solution, said hydrochloric acid and water solution being one part hydrochloric acid to six parts water;
- agitating said extracted whey for at least one hour after reaching 2.5 pH;
- after agitation, resting said extracted whey for at least one hour; and
- adding a third solution to raise the pH of the extracted whey to 4.2 pH, said third solution being a caustic sodium hydroxide and water solution, a concentration of caustic sodium hydroxide being 50%, said caustic hydroxide and water solution being one part caustic sodium hydroxide to ten parts water.

16. The process of claim 15, the steps of the process further comprising the steps of:
- filtering said extracted whey after adding said caustic hydroxide solution through a filter, said filter being a 0.2 micron filter;
- adding 2.0 grams of Ethylenediaminetetraacetic acid and 15.2 grams of sodium benzoate per 1.0 gallons of a liquid permeating said filter; and
- bottling of said liquid permeating said filter after addition of said Ethylenediaminetetraacetic acid and said sodium benzoate.

17. The process of claim 15, the steps of the process further comprising the steps of:
- cooling said adjusted whey after adding said caustic hydroxide solution to 40degrees Fahrenheit; and
- drying said adjusted whey to produce a powder.

* * * * *